US011967069B2

(12) United States Patent
Zhang et al.

(10) Patent No.: US 11,967,069 B2
(45) Date of Patent: Apr. 23, 2024

(54) PATHOLOGICAL SECTION IMAGE PROCESSING METHOD AND APPARATUS, SYSTEM, AND STORAGE MEDIUM

(71) Applicant: Tencent Technology (Shenzhen) Company Limited, Shenzhen (CN)

(72) Inventors: Jun Zhang, Shenzhen (CN); Kezhou Yan, Shenzhen (CN); Jianhua Yao, Shenzhen (CN); Xiao Han, Shenzhen (CN)

(73) Assignee: TENCENT TECHNOLOGY (SHENZHEN) COMPANY LIMITED, Shenzhen (CN)

(*) Notice: Subject to any disclaimer, the term of this patent is extended or adjusted under 35 U.S.C. 154(b) by 403 days.

(21) Appl. No.: 17/515,170

(22) Filed: Oct. 29, 2021

(65) Prior Publication Data

US 2022/0051404 A1 Feb. 17, 2022

Related U.S. Application Data

(63) Continuation of application No. PCT/CN2020/115842, filed on Sep. 17, 2020.

(30) Foreign Application Priority Data

Nov. 14, 2019 (CN) .......................... 201911115369.6

(51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06T 7/136* (2017.01); *G06T 7/187* (2017.01);
(Continued)

(58) Field of Classification Search
None
See application file for complete search history.

(56) References Cited

U.S. PATENT DOCUMENTS 9,567,651 B2* 2/2017 Seth ...................... G06V 20/695
10,055,840 B2* 8/2018 Chukka ................. G06T 7/0012
(Continued)

FOREIGN PATENT DOCUMENTS

CN 1074365 A 7/1993
CN 101560544 A 10/2009
(Continued)

OTHER PUBLICATIONS

Peng Shi, "Automated Quantitative Image Analysis of Hematoxylin-Eosin Staining Slides in Lymphoma Based on Hierarchical Kmeans Clustering", 2016 8th International Conference on Information Technology in Medicine and Education, Dec. 25, 2016, Retrieved from the Internet: https://ieeexplore.ieee.org/document/7976445.
(Continued)

*Primary Examiner* — Anand P Bhatnagar
(74) *Attorney, Agent, or Firm* — Morgan, Lewis & Bockius LLP

(57) ABSTRACT

This application provides a pathological section image processing method performed by a computer device. The method includes: obtaining stained images of a pathological section after cell membrane staining; determining cell nucleus positions of cancer cells in a stained image under an $i^{th}$ field of view in the n fields of view; generating a cell membrane description result of the stained image under the $i^{th}$ field of view, the cell membrane description result being used for indicating completeness and staining intensity of the cell membrane staining; determining quantities of cells of types in the stained image under the $i^{th}$ field of view according to the cell nucleus positions and the cell membrane description result; and determining an analysis result
(Continued)

of the pathological section according to quantities of the cells of types in the stained images under the n fields of view.

20 Claims, 6 Drawing Sheets

(51) Int. Cl.
  *G06T 7/136* (2017.01)
  *G06T 7/187* (2017.01)
  *G06T 7/70* (2017.01)
  *G06V 20/69* (2022.01)
  *G16H 10/40* (2018.01)
  *G16H 30/40* (2018.01)
  *G16H 50/20* (2018.01)
  *G16H 70/60* (2018.01)

(52) U.S. Cl.
  CPC .............. *G06T 7/70* (2017.01); *G06V 20/695* (2022.01); *G06V 20/698* (2022.01); *G16H 10/40* (2018.01); *G16H 30/40* (2018.01); *G16H 50/20* (2018.01); *G16H 70/60* (2018.01); *G06T 2207/10056* (2013.01); *G06T 2207/20036* (2013.01); *G06T 2207/30024* (2013.01); *G06T 2207/30096* (2013.01); *G06T 2207/30242* (2013.01); *G06V 2201/03* (2022.01)

(56) References Cited

U.S. PATENT DOCUMENTS

| | | | |
|---|---|---|---|
| 10,628,658 B2* | 4/2020 | Bredno | G06V 20/695 |
| 10,657,643 B2* | 5/2020 | Chukka | G06T 7/0012 |
| 11,257,301 B2* | 2/2022 | Tominaga | G01N 21/6458 |
| 11,526,984 B2* | 12/2022 | Barnes | G06T 7/11 |
| 11,721,427 B2* | 8/2023 | Barnes | G16H 30/40 |
| 2007/0020697 A1 | 1/2007 | Cualing et al. | |
| 2010/0279341 A1* | 11/2010 | Steiner | G01N 15/1433 435/40.5 |
| 2015/0086103 A1 | 3/2015 | Tsunomori et al. | |
| 2017/0103521 A1* | 4/2017 | Chukka | G06V 20/695 |
| 2017/0372117 A1* | 12/2017 | Bredno | G06T 7/00 |
| 2018/0336682 A1* | 11/2018 | Chukka | G06V 20/695 |
| 2020/0184192 A1* | 6/2020 | Tominaga | G06V 20/698 |
| 2020/0232019 A1* | 7/2020 | Erber | G01N 33/57426 |
| 2021/0201485 A1* | 7/2021 | Chukka | G06T 7/0012 |
| 2021/0285056 A1* | 9/2021 | Chukka | G06V 20/698 |
| 2023/0352151 A1* | 11/2023 | Barnes | G06V 20/698 |

FOREIGN PATENT DOCUMENTS

| | | |
|---|---|---|
| CN | 108181334 A | 6/2018 |
| CN | 108346145 A | 7/2018 |
| CN | 109215017 A | 1/2019 |
| CN | 109903284 A | 6/2019 |
| CN | 110021013 A | 7/2019 |
| CN | 110363762 A | 10/2019 |
| CN | 110390676 A | 10/2019 |
| CN | 110853022 A | 2/2020 |
| WO | WO 2014088049 A1 | 6/2014 |
| WO | WO 2014102130 A1 | 7/2014 |

OTHER PUBLICATIONS

Tencent Technology, ISR, PCT/CN2020/115842, dated Dec. 23, 2020, 3 pgs.

Kan Xianxiang et al., "Study on Segmentation of Cancer Nests and Interstitium of Histopathological Images of Breast Cancer with HE Staining", Computer Engineering and Science, Feb. 28. 2017, Retrieved from the Internet: http://www.corc.ac.en/handle/1471x/4071624?mode=full.

Tencent Technology, WO, PCT/CN2020/115842, Dec. 23, 2020, 5 pgs.

Tencent Technology, IPRP, PCT/CN2020/115842, dated May 17, 2022, 6 pgs.

Jun Zhang et al., "Microscope Based HER2 Scoring System", Arxiv.Org, Cornell University Library, 14853, Sep. 15, 2020, XP081763220, 11 pgs.

Tencent Technology, European Office Action, EP Patent Application No. 20887251.5, dated Apr. 24, 2023, 8 pgs.

Extended European Search Report, EP20887251.5, dated Jul. 25, 2022, 12 pgs.

* cited by examiner

PATHOLOGICAL SECTION IMAGE PROCESSING METHOD AND APPARATUS, SYSTEM, AND STORAGE MEDIUM

CROSS-REFERENCE TO RELATED APPLICATIONS

This application is a continuation application of PCT Patent Application No. PCT/CN2020/115842, entitled "PATHOLOGICAL SECTION IMAGE PROCESSING METHOD. APPARATUS, SYSTEM, AND STORAGE MEDIUM" filed on Sep. 17, 2020, which claims priority to Chinese Patent Application No. 201911115369.6, filed with the State Intellectual Property Office of the People's Republic of China on Nov. 14, 2019, and entitled "PATHOLOGICAL SECTION IMAGE PROCESSING METHOD AND APPARATUS, SYSTEM, AND STORAGE MEDIUM", all of which are incorporated herein by reference in their entirety.

FIELD OF THE TECHNOLOGY

Embodiments of this application relate to the field of intelligent medical technologies of artificial intelligence (AI), and in particular, to a pathological section image processing method and apparatus, a system, and a storage medium.

BACKGROUND OF THE APPLICATION

The correct detection and evaluation of the human epidermal growth factor receptor-2 (HER2) protein expression and gene amplification status of breast cancer is critical to the clinical treatment and prognosis of breast cancer.

In the related art, cell membrane staining is performed on a pathological section, and the pathological section after the cell membrane staining is then observed and analyzed under a microscope, to assist doctors in HER2 detection. However, there is a lack of systematic cell membrane staining analysis on pathological sections in the related art, resulting in inaccurate final detection results.

SUMMARY

Embodiments of this application provide a pathological section image processing method and apparatus, a system, and a storage medium, which can be used to resolve a technical problem of inaccurate analysis of pathological sections in the related art. The technical solutions are as follows:

According to an aspect, an embodiment of this application provides a pathological section image processing method performed by a computer device, the method including:
  obtaining stained images of a pathological section, wherein each stained image is generated from a respective one of n fields of view of the pathological section under a microscope after cell membrane staining, n being a positive integer;
  determining cell nucleus positions of cancer cells in a stained image under an $i^{th}$ field of view in then fields of view, i being a positive integer less than or equal to n;
  generating a cell membrane description result of the stained image under the $i^{th}$ field of view, the cell membrane description result being used for indicating completeness and staining intensity of the cell membrane staining;
  determining quantities of cells of types in the stained image under the $i^{th}$ field of view according to the cell nucleus positions and the cell membrane description result; and
  determining an analysis result of the pathological section according to the quantities of the cells of types in the stained images under the n fields of view.

According to still another aspect, an embodiment of this application provides a computer device, including a processor and a memory, the memory storing at least one program, the at least one program being loaded and executed by the processor to implement the foregoing pathological section image processing method.

According to yet another aspect, an embodiment of this application provides a non-transitory computer-readable storage medium, storing at least one program, the at least one program being loaded and executed by a processor to implement the foregoing pathological section image processing method.

The technical solutions provided in the embodiments of this application may include the following beneficial effects:
  Stained images of a pathological section are obtained, each stained image being generated from a respective one of n fields of view of the pathological section under a microscope after cell membrane staining, n being a positive integer, and cell nucleus detection and cell membrane description are performed on each stained image, to obtain cell nucleus positions and a cell membrane description result of cancer cells in each stained image. The two aspects of information are combined to determine quantities of cells of types, and further determine an analysis result of the pathological section. Therefore, a technical solution for systematic cell membrane staining analysis on a pathological section is provided, to improve the accuracy of a detection result.

In addition, in the technical solutions provided in the embodiments of this application, a deep learning method is not directly used to directly analyze a stained image of a pathological section, and an analysis result is directly outputted by a model. Such a black box processing manner does not conform to relevant diagnostic guidelines for HER2 grading. In the technical solutions provided in the embodiments of this application, cancer cells are detected and classified according to the definition of the relevant diagnostic guidelines, so that the HER2 grading can be performed according to the determining criteria of the guidelines, thereby improving the standardization and accuracy of a final HER2 grading results.

BRIEF DESCRIPTION OF THE DRAWINGS

To describe technical solutions in embodiments of this application more clearly, the following briefly introduces the accompanying drawings required for describing the embodiments. Apparently, the accompanying drawings in the following description show only some embodiments of this application, and a person of ordinary skill in the art may still derive other accompanying drawings from these accompanying drawings without creative efforts.

DESCRIPTION OF EMBODIMENTS

Figure 1:
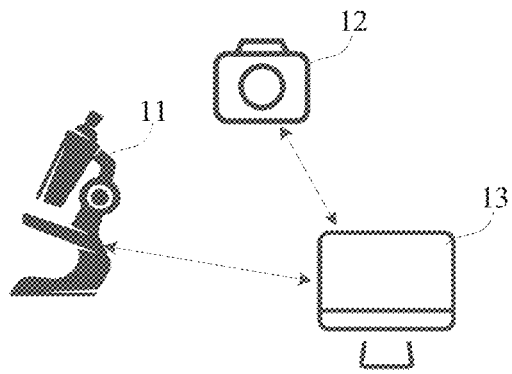
FIG. 1 is a schematic diagram of an intelligent microscope system according to an embodiment of this application.

To make objectives, technical solutions, and advantages of this application clearer, the following further describes implementations of this application in detail with reference to the accompanying drawings.

Artificial Intelligence (AI) is a theory, method, technology, and application system that use a digital computer or a machine controlled by a digital computer to simulate, extend, and expand human intelligence, perceive the environment, obtain knowledge, and use the knowledge to obtain the best result. In other words, AI is a comprehensive technology of computer science, which attempts to understand essence of intelligence and produces a new intelligent machine that responds in a manner similar to human intelligence. AI is to study design principles and implementation methods of various intelligent machines, so that the machines have the functions of perception, reasoning, and decision-making.

The AI technology is a comprehensive discipline, covering a wide range of fields including both hardware-level technologies and software-level technologies. The basic AI technology generally includes technologies such as sensors, dedicated AI chips, cloud computing, distributed storage, big data processing technologies, operating/interaction systems, and mechatronics. AI software technologies mainly include a computer vision technology, a speech processing technology, a natural language processing technology, machine learning/deep learning, and the like.

Computer vision (CV) is a science that studies how to enable a machine to "see", and to be specific, to implement machine vision such as recognition, tracking, measurement, and the like for a target by using a camera and a computer in replacement of human eyes, and further perform graphic processing, so that the computer processes the target into an image more suitable for human eyes to observe, or more suitable to be transmitted to an instrument for detection. As a scientific subject, CV studies related theories and technologies, and attempts to establish an AI system that can obtain information from images or multidimensional data. The CV technologies generally include technologies such as image processing, image recognition, image semantic understanding, image retrieval, optical character recognition (OCR), video processing, video semantic understanding, video content/behavior recognition, three-dimensional (3D) object reconstruction, a 3D technology, virtual reality, augmented reality, synchronous positioning, and map construction, and further include biometric feature recognition technologies such as common face recognition and fingerprint recognition.

Machine learning (ML) is a multi-field interdisciplinary subject involving the probability theory, statistics, the approximation theory, convex analysis, the algorithm complexity theory, and the like. ML specializes in studying how a computer simulates or implements a human learning behavior to obtain new knowledge or skills, and reorganize an existing knowledge structure, so as to keep improving its performance. ML is the core of AI, is a basic way to make the computer intelligent, and is applied to various fields of AI. ML and deep learning generally include technologies such as an artificial neural network, a belief network, reinforcement learning, transfer learning, inductive learning, and learning from demonstrations.

With the research and progress of the AI technology, the AI technology is studied and applied in a plurality of fields such as a common smart home, a smart wearable device, a virtual assistant, a smart speaker, smart marketing, unmanned driving, automatic driving, an unmanned aerial vehicle, a robot, smart medical care, and smart customer service. It is believed that with the development of technologies, the AI technology will be applied to more fields, and play an increasingly important role.

The solutions provided in the embodiments of this application relate to the field of intelligent medical technologies. The CV technology is used to perform image processing and analysis on a pathological section after cell membrane staining, to finally determine an analysis result corresponding to the pathological section, thereby assisting doctors in diseases diagnosis and treatment.

The technical solutions of this application are described below by using several embodiments.

FIG. 1 is a schematic diagram of an intelligent microscope system according to an embodiment of this application. The intelligent microscope system may include: a microscope 11, a camera 12, and a computer device 13.

The microscope 11 is configured to observe a pathological section. In the embodiments of this application, the microscope 11 is configured to observe a pathological section after cell membrane staining.

The camera 12 is configured to capture and obtain a pathological section image of the pathological section under a field of view of the microscope 11. In some embodiments, the pathological section is an HER2 stained section. HER2 staining stains a membrane of a positive cancer cell brown and a nucleus thereof blue. HER2 is generally graded into four categories: 0, 1+, 2+, and 3+. Generally, the pathological section image needs to be acquired under a medium-high-power field of view of the microscope (such as 10 times, 20 times, or 40 times).

The computer device 13 is configured to obtain an analysis result corresponding to the pathological section image by executing a method procedure described in detail later based on the pathological section image captured by the camera 12. In the case that the pathological section is a HER2 stained section, the analysis result may be an HER2 grading result. The computer device 13 may be any electronic device with computing and storage capabilities, such as a personal computer (PC).

The microscope 11, the camera 12, and the computer device 13 may be configured at the same physical position, or even configured in the same physical device. Alternatively, the microscope 11, the camera 12, and the computer device 13 may be configured at different positions, which are connected through a wired or wireless communication network to transmit data or commands between each other.

Figure 2:
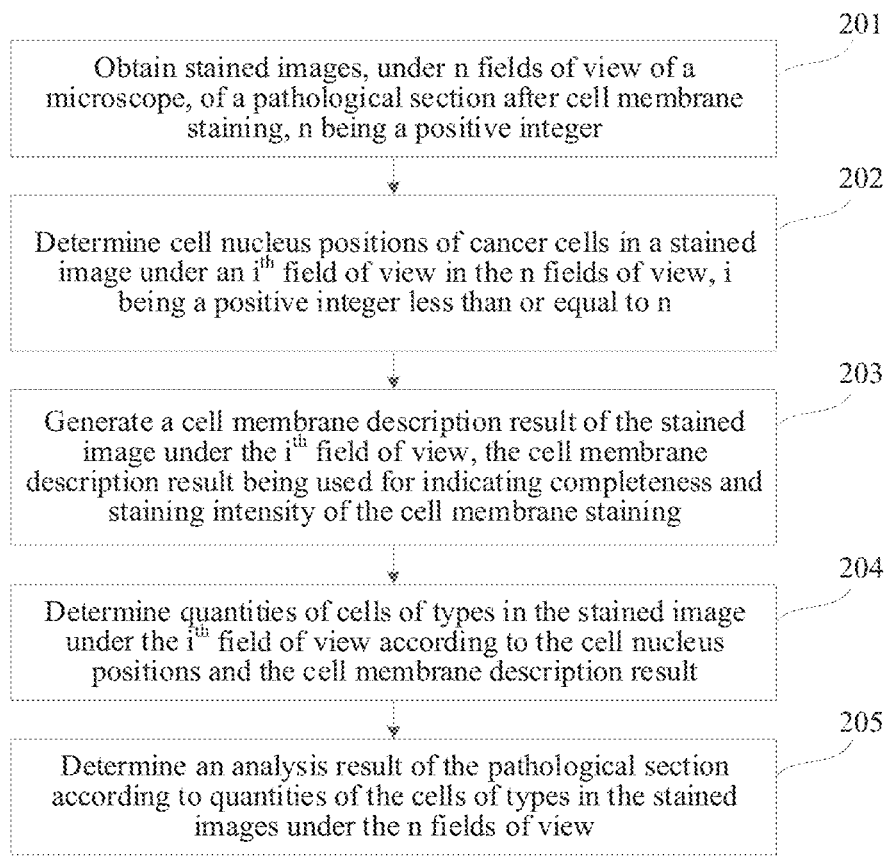
FIG. 2 is a flowchart of a pathological section image processing method according to an embodiment of this application.

FIG. 2 is a flowchart of a pathological section image processing method according to an embodiment of this application. The execution entity of each step of the method may be the computer device in the intelligent microscope system described above. The method may include the following steps:

Step 201: Obtain stained images of a pathological section, wherein each stained image is generated from a respective one of n fields of view of the pathological section under a microscope after cell membrane staining, n being a positive integer.

In some embodiments, then fields are a plurality of microscope fields including cancer cells obtained after observing the pathological section. The n fields may be selected by a doctor. For example, determining of HER2 grading of the pathological section is used as an example. Because the HER2 grading is defined on a staining status of infiltrated cancer cells, the doctor may be responsible for acquiring a plurality of microscope fields that typically include regions of the infiltrated cancer cells.

In an example, n is an integer greater than 1, for example, n is 10. Because the HER2 grading in relevant diagnostic guidelines (for example, breast cancer HER2 detection guidelines) is defined based on full-section analysis of the pathological section, but images in a microscope application scenario are obtained from a plurality of fields of view, it is difficult to splice a complete pathological section image. In this application, the HER2 grading is performed by adopting the strategy of using a plurality of typical field images selected by the doctor to approximately replace a full-section diagnosis result, which can avoid full-section scan and obtain an accurate HER2 grading result.

Figure 3:
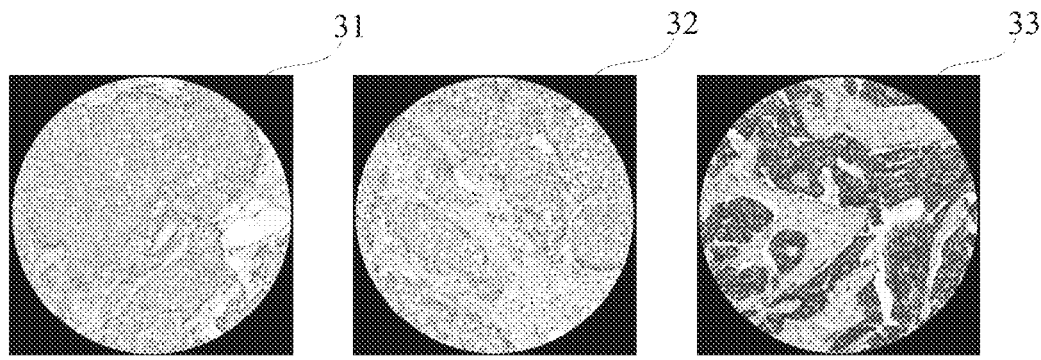
FIG. 3 is a schematic diagram of stained images under a plurality of fields of view of a microscope according to this application.

For example, FIG. 3 is a schematic diagram of stained images, under a plurality of fields of view of a microscope, of a pathological section after cell membrane staining, where images 31, 32, and 33 each represent a stained image of a same pathological section under three fields of view of a microscope. The stained image is actually an RGB image, on which a membrane of a positive cancer cell is stained brown and a nucleus thereof is stained blue.

Step 202: Determine cell nucleus positions of cancer cells in a stained image under an $i^{th}$ field of view in the n fields of view, i being a positive integer less than or equal to n.

In an exemplary embodiment, a deep learning method may be used to perform cancer cell detection on a stained image to determine cell nucleus positions of cancer cells in the stained image. For example, a fully convolutional network (FCN) may be used to construct a cell nucleus detection model, the cell nucleus detection model may be trained by heat map regression, and the trained cell nucleus detection model may be used for nucleus detection. An input of the cell nucleus detection model may be a stained image (the stained image is an RGB image), and the input is a Gauss-like response image centered on a cell center point. All cancer cells can be obtained by searching for a local maximum response position of an inputted heat map.

Figure 4:
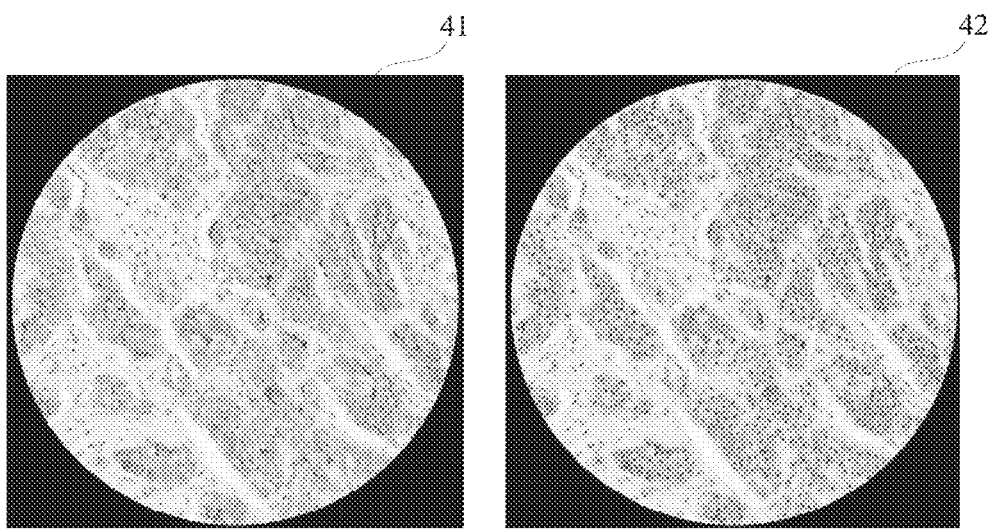
FIG. 4 is a schematic diagram of input and output of a cell nucleus detection model according to this application.

In some embodiments, the stained image under the $i^{th}$ field of view is processed by using the cell nucleus detection model to obtain the cell nucleus positions of the cancer cells in the stained image under the $i^{th}$ field of view. The cell nucleus positions may include a coordinate set (marked as Ddetect) of the cancer cells in the stained image under the $i^{th}$ field of view, where the coordinate set Ddetect includes position coordinates of the sell nuclei of the cancer cells in the stained image under the $i^{th}$ field of view. For example, as shown in FIG. 4, an input image 41 of the cell nucleus detection model is on the left side, that is, a stained image under a certain field of view, and a stained image 42 on which cell nucleus positions of detected cancer cells are marked is on the right side, where the cell nucleus positions are marked with small black dots.

Certainly, the cancer cell detection method described above is only exemplary and explanatory, and the embodiments of this application are not limited to other cancer cell detection methods.

Step 203: Generate a cell membrane description result of the stained image under the $i^{th}$ field of view, the cell membrane description result being used for indicating completeness and staining intensity of the cell membrane staining.

Because the completeness and staining intensity of cell membrane staining determine an analysis result of the pathological section, the cell membrane description result of the stained image needs to be obtained. The completeness of cell membrane staining refers to whether a stained cell membrane is a complete cell membrane, and the staining intensity refers to a staining depth of the stained cell membrane.

In this embodiment of this application, a stained image may be processed and analyzed to obtain a cell membrane description result of the stained image. For the related process, reference may be made to the description in the following embodiments.

Step 204: Determine quantities of cells of types in the stained image under the $i^{th}$ field of view according to the cell nucleus positions and the cell membrane description result.

In this embodiment of this application, cells are classified into a plurality of types according to cell membrane staining. In some embodiments, the types include: completely and strongly stained cells, incompletely and strongly stained cells, completely and weakly stained cells, incompletely and weakly stained cells, and non-stained cells. The completely and strongly stained cells refer to cells with complete cell membrane staining and high staining intensity, the incompletely and strongly stained cells refer to cells with incomplete cell membrane staining and high staining intensity, the completely and weakly stained cells refer to cells with complete cell membrane staining and low staining intensity, the incompletely and weakly stained cells refer to cells with incomplete cell membrane staining and low staining intensity, and non-stained cells refer to cells not stained.

By combining cell nucleus positions and a cell membrane description result of a stained image, quantities of cells of types in the stained image may be determined, to implement quantitative analysis and determining of the cells. For example, it is determined that quantities of cells of types in a stained image under a certain field of view include: 170 completely and strongly stained cells, 230 incompletely and strongly stained cells, 2 completely and weakly stained cells, 104 incompletely and weakly stained cells, and 47 non-stained cells.

Step 205: Determine an analysis result of the pathological section according to quantities of the cells of types in the stained images under the n fields of view.

When n is an integer greater than 1, for a stained image under each of the plurality of fields of view, the foregoing steps 202 to 204 may be performed, to obtain quantities of cells of types in the stained image in each field of view. The quantities of the cells of types in the stained images under then fields of view are then comprehensively counted. For each type of cell, quantities of the each type of cell in the foregoing stained images are summed to obtain a total quantity of the each type of cell in all the n stained images.

In some embodiments, proportions of the cells of types in the stained images under the n fields of view are determined according to the quantities of the cells of types in the stained images under the n fields of view; and the analysis result of the pathological section is determined according to the proportions of the cells of types. An example is used in which HER2 grading is performed on a breast cancer pathological section. If a proportion of completely and strongly stained cells is greater than 10%, an HER2 grade is 3+. If a proportion of completely and weakly stained cells is greater than 10% or the proportion of completely and strongly stained cells is less than or equal to 10%, the HER2 grade is 2+. If a proportion of incompletely and weakly stained cells is greater than 10%, the HER2 grade is 1+. If a proportion of non-stained cells or incompletely and weakly stained cells is less than or equal to 10%, the HER2 grade is 0+. When the HER2 grade is 3+, it is determined as HAR2 positive. When the HER2 grade is 2+, a method of in situ hybridization needs to be further used to perform HER2 gene expansion status detection, or different tissue blocks may be selected for re-detection. When the HER2 grade is 1+ or 0, it is determined as HAR2 negative. Certainly, the foregoing description of determining the analysis result of the pathological section according to the proportions of the cells of types is only exemplary and explanatory. In practical applications, the corresponding analysis result determining standards may be set in combination with actual situations, and this is not limited in this embodiment of this application.

Based on the above, according to the technical solution provided in this embodiment of this application, stained images of a pathological section are obtained, each stained image being generated from a respective one of n fields of view of the pathological section under a microscope after cell membrane staining, n being a positive integer, and cell nucleus detection and cell membrane description are performed on each stained image, to obtain cell nucleus positions and a cell membrane description result of cancer cells in each stained image. The two aspects of information are combined to determine quantities of cells of types, and further determine an analysis result of the pathological section. Therefore, a technical solution for systematic cell membrane staining analysis on a pathological section is provided, which helps to improve the accuracy of a detection result.

In addition, in the technical solutions provided in the embodiments of this application, a deep learning method is not directly used to directly analyze a stained image of a pathological section, and an analysis result is directly outputted by a model. Such a black box processing manner does not conform to relevant diagnostic guidelines for HER2 grading. In the technical solutions provided in the embodiments of this application, cancer cells are detected and classified according to the definition of the relevant diagnostic guidelines, so that the HER2 grading can be performed according to the determining criteria of the guidelines, thereby improving the standardization and accuracy of a final HER2 grading results.

In an exemplary embodiment, step 203 may include the following sub-steps:

1. Perform color channel decomposition and recombination on the stained image under the $i^{th}$ field of view to obtain a target stained channel image;

The stained image is an RGB three-channel image, and may be expressed as IRGB. The color channel decomposition and recombination are performed on the stained image IRGB, to generate three immunohistochemical channel image, namely, IH (hematoxylin) and IE (eosin), and IDAB (Diaminobenzidine), where an IDAB channel image is a brown stained channel image. In this embodiment of this application, the target stained channel image is the brown stained channel image, and an expected cell membrane description result can be obtained by analyzing the brown stained channel image.

2. Generate the cell membrane description result according to the target stained channel image.

In this embodiment of this application, the cell membrane description result includes a first region segmentation result, a second region segmentation result, and a third region segmentation result. The first region segmentation result is used for indicating positions of cell membranes with complete staining, the second region segmentation result is used for indicating positions of cell membranes whose staining intensities are greater than a first limit value, and the third region segmentation result is used for indicating positions of cell membranes whose staining intensities are greater than a second limit value. If a larger value of a staining intensity indicates a higher staining intensity, the first limit value is less than the second limit value, that is, cells whose staining intensities are greater than the first limit value and less than or equal to the second limit value are weakly stained cells, cells whose staining intensities are greater than the second limit value are strongly stained cells, and cells whose staining intensities are less than the first limit value may be considered as non-stained cells.

In some embodiments, this step may include the following several sub-steps:

2.1. Perform threshold segmentation processing on the target stained channel image by using a first threshold, to obtain a weakly-stained segmented image;

For example, for each pixel in the target stained channel image, if a pixel value of the pixel is greater than the first threshold, the pixel value of the pixel is recorded as 1, and if the pixel value of the pixel is less than or equal to the first threshold, the pixel value of the pixel is recorded as 0. Finally, the target stained channel image is converted into a binary weakly-stained segmented image. The first threshold may be preset in combination with actual situations, and this is not limited in this embodiment of this application.

2.2. Perform threshold segmentation processing on the target stained channel image by using a second threshold, to obtain a strongly-stained segmented image;

For example, for each pixel in the target stained channel image, if a pixel value of the pixel is greater than the second threshold, the pixel value of the pixel is recorded as 1, and if the pixel value of the pixel is less than or equal to the second threshold, the pixel value of the pixel is recorded as 0. Finally, the target stained channel image is converted into a binary strongly-stained segmented image. The second threshold may be preset in combination with actual situations, and this is not limited in this embodiment of this application.

2.3. Generate the cell membrane description result according to the weakly-stained segmented image and the strongly-stained segmented image.

The target stained channel image being the foregoing IDAB channel image is used as an example. Because a pixel value of each pixel in the IDAB channel image is a negative number, a first threshold t1 may be used to perform threshold segmentation processing on the image IDAB to obtain a weakly-stained segmented image Mlight, and a second threshold t2 may be used to perform threshold segmentation processing on the image IDAB to obtain a strongly-stained segmented image Mheavy, where t2=a×t1, and a is a coefficient less than 1. For example, t1=−0.35, and a=0.9.

The weakly-stained segmented image includes not only weakly stained cells but also strongly stained cells that are stronger than being weakly stained, but the strongly-stained segmented image includes only strongly stained cells.

In some embodiments, after the weakly-stained segmented image and the strongly-stained segmented image are obtained, first morphological processing may be performed on the weakly-stained segmented image to obtain the first region segmentation result; second morphological processing may be performed on the weakly-stained segmented image to obtain the second region segmentation result; and the second morphological processing may be performed on the strongly-stained segmented image to obtain the third region segmentation result.

Figure 5:
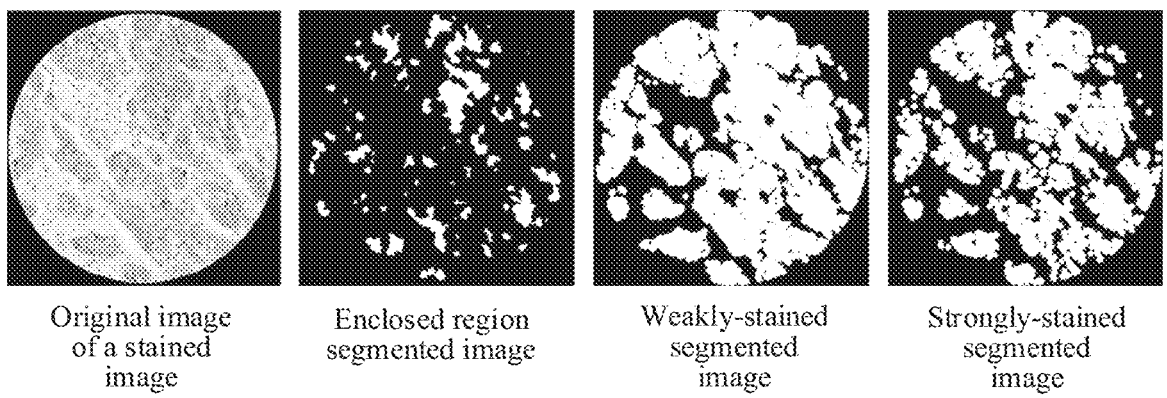
FIG. 5 is a schematic diagram of an original image of a stained image, an enclosed region segmented image, a weakly-stained segmented image, and a strongly-stained segmented image according to this application.

The performing first morphological processing on the weakly-stained segmented image includes: performing cytoskeleton extraction processing on the weakly-stained segmented image to obtain a cytoskeleton in the weakly-stained segmented image; searching for an enclosed region in which the cytoskeleton is closed; filling, when the enclosed region is an innermost-layer enclosed region, the innermost-layer enclosed region to obtain an enclosed region segmented image; and extracting position information of foreground pixels in the enclosed region segmented image to obtain the first region segmentation result. In some embodiments, centerline extraction processing is performed on the weakly-stained segmented image Mlight, cell membrane delineation is performed to obtain the cytoskeleton, and statistical analysis is performed on the centerline to count the enclosed region formed by each connected boundary. If the enclosed region is an innermost-layer enclosed region, the innermost-layer enclosed region is determined as a delineated boundary of a complete cell membrane. All innermost-layer enclosed regions are filled to obtain an enclosed region segmented image Menclosed, as shown in FIG. 5, and a position coordinate set of all foreground pixels in the enclosed region segmented image Menclosed is defined as Penclosed, where Penclosed is the first region segmentation result.

The performing second morphological processing on the weakly-stained segmented image includes: performing region expansion processing on the weakly-stained segmented image to obtain a processed weakly-stained segmented image; and extracting position information of foreground pixels in the processed weakly-stained segmented image to obtain the second region segmentation result. An expansion distance d of the region expansion processing may be preset in combination with actual situations, for example, d=45, and this is not limited in this embodiment of this application. As shown in FIG. 5, it is assumed that region expansion processing is performed on the weakly-stained segmented image Mlight to obtain a processed weakly-stained segmented image Elight, and a position coordinate set of all foreground pixels in the processed weakly-stained segmented image Elight is defined as Plight, where Plight is the second region segmentation result.

The performing the second morphological processing on the strongly-stained segmented image includes: performing region expansion processing on the strongly-stained segmented image to obtain a processed strongly-stained segmented image; and extracting position information of foreground pixels in the processed strongly-stained segmented image to obtain the third region segmentation result. An expansion distance d of the region expansion processing may be preset in combination with actual situations, for example, d=45, and this is not limited in this embodiment of this application. As shown in FIG. 5, it is assumed that region expansion processing is performed on the strongly-stained segmented image Mheavy to obtain a processed strongly-stained segmented image Eheavy, and a position coordinate set of all foreground pixels in the processed strongly-stained segmented image Eheavy is defined as Pheavy, where Pheavy is the third region segmentation result.

Correspondingly, the determining quantities of cells of types in the stained image under the $i^{th}$ field of view according to the cell nucleus positions and the cell membrane description result includes the flowing sub-steps:

1. Determine a quantity of elements in an intersection among the cell nucleus positions, the first region segmentation result, and the third region segmentation result as a quantity of the completely and strongly stained cells;

That is, a coordinate set of the completely and strongly stained cells is Ddetect∩Penclosed∩Pheavy, and the quantity of the corresponding cells is a quantity of elements in the set, namely, card(Ddetect∩Penclosed∩Pheavy).

2. Determine a quantity of elements in an intersection among the cell nucleus positions, a complementary set of the first region segmentation result with respect to the stained image under the $i^{th}$ field of view, and the second region segmentation result as a quantity of the incompletely and strongly stained cells;

That is, a coordinate set of the incompletely and strongly stained cells is Ddetect∩CUPenclosed∩Pheavy, where CUPenclosed is a complement of Penclosed to the full image U (that is, the stained image under the $i^{th}$ field of view). The quantity of the corresponding cells is card (Ddetect∩CUPenclosed∩Pheavy).

3. Determine a quantity of elements in an intersection among the cell nucleus positions, the first region segmentation result, a complementary set of the third region segmentation result with respect to the stained image under the $i^{th}$ field of view, and the second region segmentation result as a quantity of the completely and weakly stained cells;

That is, a coordinate set of the completely and weakly stained cells is Ddetect∩Penclosed∩CUPheavy∩Plight, where CUPheavy is a complement of Pheavy to the full image U (that is, the stained image under the $i^{th}$ field of view). The quantity of the corresponding cells is card (Ddetect∩Penclosed∩CUPheavy∩Plight).

4. Determine a quantity of elements in an intersection among the cell nucleus positions, the complementary set of the first region segmentation result with respect to the stained image under the $i^{th}$ field of view, the complementary set of the third region segmentation result with respect to the stained image under the $i^{th}$ field of view, and the second region segmentation result as a quantity of the incompletely and weakly stained cells;

That is, a coordinate set of the incompletely and weakly stained cells is Ddetect∩CUPenclosed∩CUPheavy∩Plight. The quantity of the corresponding cells is card(Ddetect∩CUPenclosed∩CUPheavy∩Plight).

5. Determine a quantity of elements in an intersection between the cell nucleus positions and a complementary set of the second region segmentation result with respect to the stained image under the $i^{th}$ field of view as a quantity of the non-stained cells.

That is, a coordinate set of the non-stained cells is Ddetect∩CUPlight, where CUPlight is a complement of Plight to the full image U (that is, the stained image under the $i^{th}$ field of view). The quantity of the corresponding cells is card(Ddetect∩CUPlight).

In this embodiment of this application, by using the foregoing methods, quantitative statistics and analysis are performed on the various cell types in the stained images of the pathological section, thereby providing reliable data support for HER2 grading.

Figure 6:
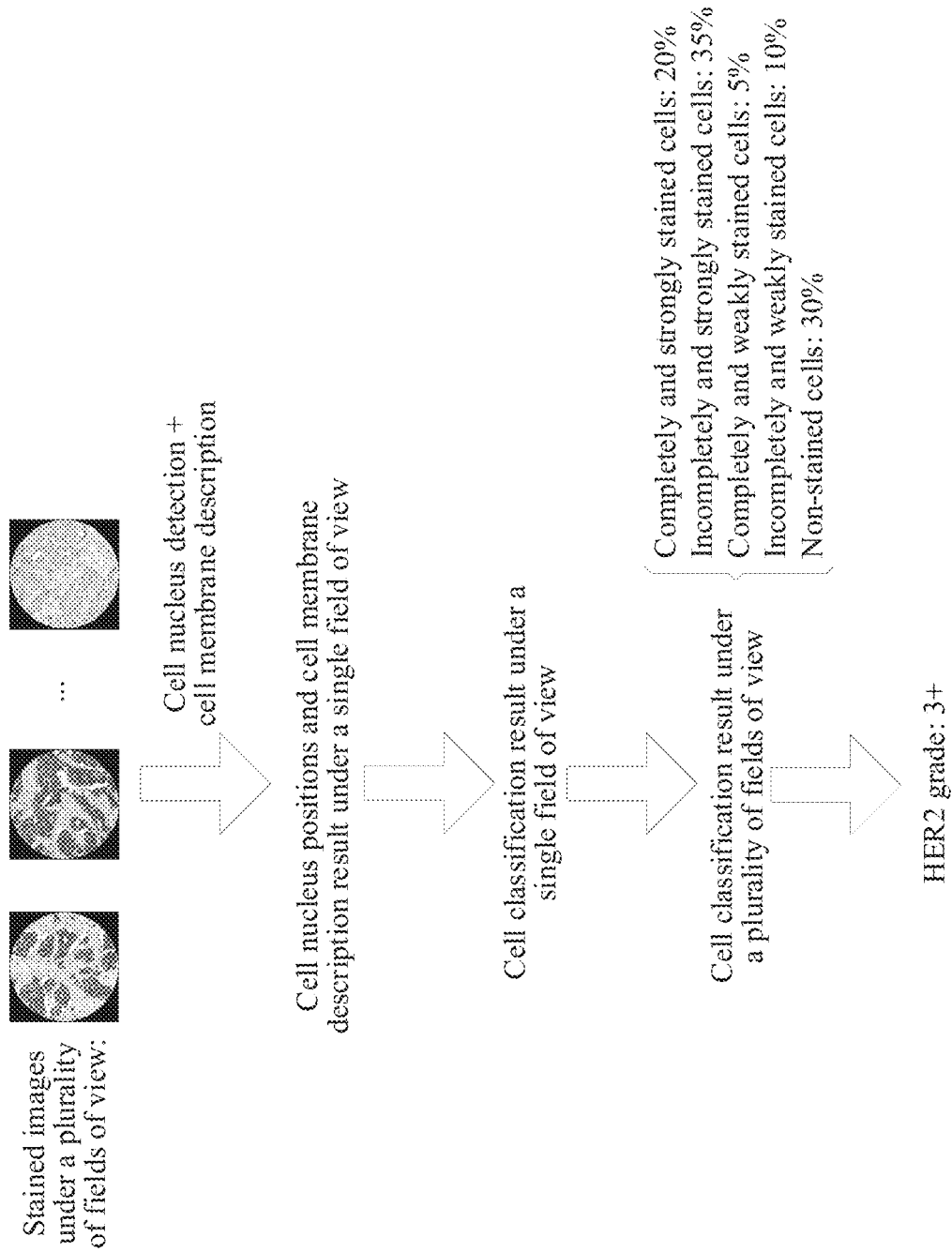
FIG. 6 is a flowchart of a complete technical solution according to this application.

FIG. 6 is a flowchart of a complete technical solution according to this application. Stained images of a pathological section after cell membrane staining under a plurality of fields of view of a microscope are obtained, and cell nucleus detection and cell membrane description are performed on a stained image under a single field of view, to obtain cell nucleus positions and a cell membrane description result of cancer cells in the stained image under the single field of view. The two aspects of information are combined to obtain a cell classification result under the single field of view, that is, quantities of cells of types. The cell classification results under each single field of view are combined to obtain a cell classification result under a plurality of fields of view, and the HER2 grade corresponding to the pathological section is then determined according to the cell classification result. For example, the cell classification result under the plurality of fields of view is: 20% of completely and strongly stained cells, 35% of incompletely and strongly stained cells, 5% of completely and weakly stained cells, 10% of incompletely and weakly stained cells, and 30% of non-stained cells. In this case, the HER2 grade is 3+.

The following is an apparatus embodiment of this application, which may be used for performing the method embodiments of this application. For details not disclosed in the apparatus embodiment of this application, reference may be made to the method embodiments of this application.

Figure 7:
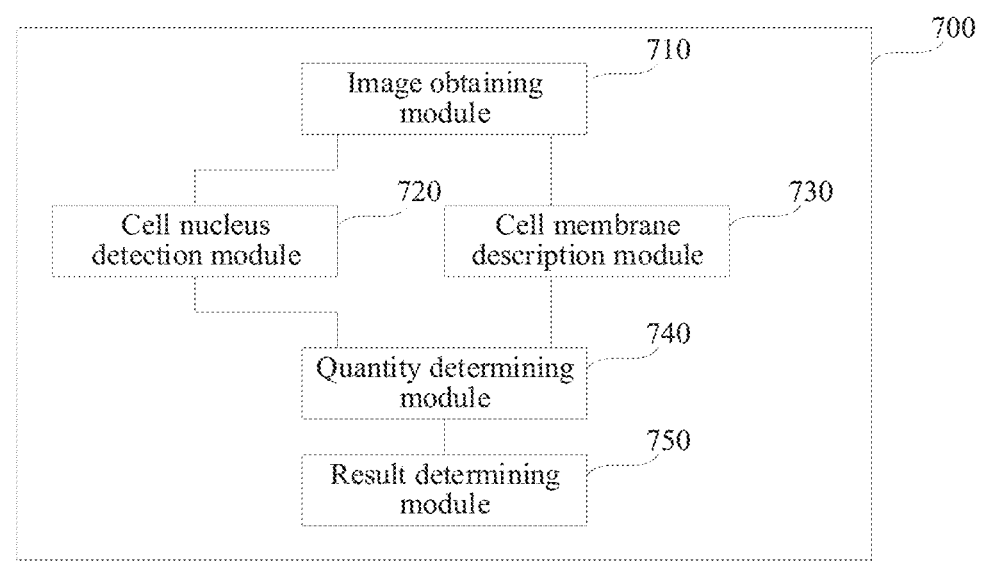
FIG. 7 is a block diagram of a pathological section image processing apparatus according to an embodiment of this application.

FIG. 7 is a block diagram of a pathological section image processing apparatus according to an embodiment of this application. The apparatus has functions of implementing the foregoing method embodiments. The functions may be implemented by hardware, or may be implemented by hardware executing corresponding software. The apparatus may be the computer device described above, or may be disposed in the computer device. The apparatus 700 may include: an image obtaining module 710, a cell nucleus detection module 720, a cell membrane description module 730, a quantity determining module 740, and a result determining module 750.

The image obtaining module 710 is configured to obtain stained images of a pathological section, wherein each stained image is generated from a respective one of n fields of view of the pathological section under a microscope after cell membrane staining, n being a positive integer.

The cell nucleus detection module 720 is configured to determine cell nucleus positions of cancer cells in a stained image under an $i^{th}$ field of view in the n fields of view, i being a positive integer less than or equal to n.

The cell membrane description module 730 is configured to generate a cell membrane description result of the stained image under the $i^{th}$ field of view, the cell membrane description result being used for indicating completeness and staining intensity of the cell membrane staining.

The quantity determining module 740 is configured to determine quantities of cells of types in the stained image under the $i^{th}$ field of view according to the cell nucleus positions and the cell membrane description result.

The result determining module 750 is configured to determine an analysis result of the pathological section according to quantities of the cells of types in the stained images under the n fields of view.

Based on the above, according to the technical solution provided in this embodiment of this application, stained images of a pathological section after cell membrane staining under n fields of view of a microscope are obtained, and cell nucleus detection and cell membrane description are performed on each stained image, to obtain cell nucleus positions and a cell membrane description result of cancer cells in each stained image. The two aspects of information are combined to determine quantities of cells of types, and further determine an analysis result of the pathological section. Therefore, a technical solution for systematic cell membrane staining analysis on a pathological section is provided, which helps to improve the accuracy of a detection result.

Figure 8:
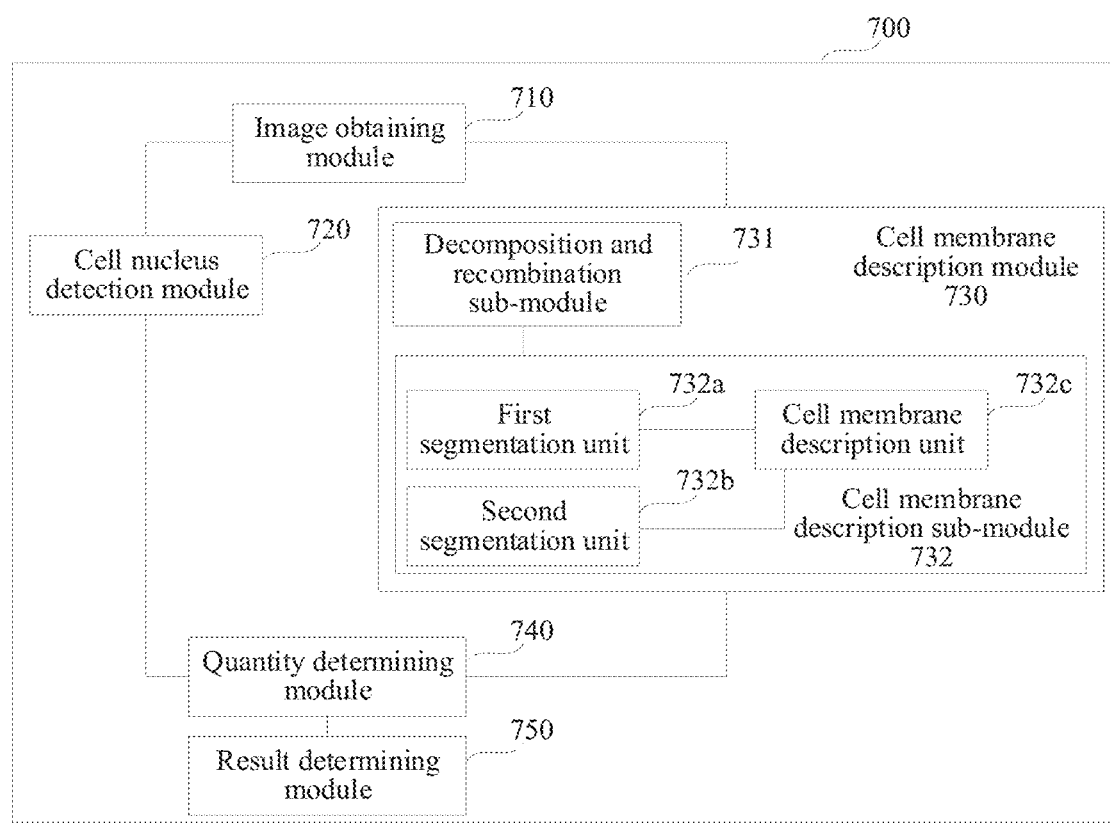
FIG. 8 is a block diagram of a pathological section image processing apparatus according to another embodiment of this application.

In an exemplary embodiment, as shown in FIG. 8, the cell membrane description module 730 includes: a decomposition and recombination sub-module 731 and a cell membrane description sub-module 732.

The decomposition and recombination sub-module 731 is configured to perform color channel decomposition and recombination on the stained image under the $i^{th}$ field of view to obtain a target stained channel image.

The cell membrane descriptionسub-module 732 is configured to generate the cell membrane description result according to the target stained channel image, the cell membrane description result including a first region segmentation result, a second region segmentation result, and a third region segmentation result, where the first region segmentation result being used for indicating positions of cell membranes with complete staining, the second region segmentation result being used for indicating positions of cell membranes whose staining intensities are greater than a first limit value, and the third region segmentation result being used for indicating positions of cell membranes whose staining intensities are greater than a second limit value.

In an exemplary embodiment, as shown in FIG. 8, the cell membrane description sub-module 732 includes: a first segmentation unit 732a, a second segmentation unit 732b, and a cell membrane description unit 732c.

The first segmentation unit 732a is configured to perform threshold segmentation processing on the target stained channel image by using a first threshold, to obtain a weakly-stained segmented image.

The second segmentation unit 732b is configured to perform threshold segmentation processing on the target stained channel image by using a second threshold, to obtain a strongly-stained segmented image.

The cell membrane description unit 732c is configured to generate the cell membrane description result according to the weakly-stained segmented image and the strongly-stained segmented image.

In an exemplary embodiment, as shown in FIG. 8, the cell membrane description unit 732c is configured to:
  perform first morphological processing on the weakly-stained segmented image to obtain the first region segmentation result;
  perform second morphological processing on the weakly-stained segmented image to obtain the second region segmentation result; and
  perform the second morphological processing on the strongly-stained segmented image to obtain the third region segmentation result.

In an exemplary embodiment, the cell membrane description unit 732c is configured to:

perform cytoskeleton extraction processing on the weakly-stained segmented image to obtain a cytoskeleton in the weakly-stained segmented image;

search for an enclosed region in which the cytoskeleton is closed;

fill, when the enclosed region is an innermost-layer enclosed region, the innermost-layer enclosed region to obtain an enclosed region segmented image; and extract position information of foreground pixels in the enclosed region segmented image to obtain the first region segmentation result.

In an exemplary embodiment, the cell membrane description unit 732c is configured to:

perform region expansion processing on the weakly-stained segmented image to obtain a processed weakly-stained segmented image; and extract position information of foreground pixels in the processed weakly-stained segmented image to obtain the second region segmentation result.

In an exemplary embodiment, the cell membrane description unit 732c is configured to:

perform region expansion processing on the strongly-stained segmented image to obtain a processed strongly-stained segmented image; and extract position information of foreground pixels in the processed strongly-stained segmented image to obtain the third region segmentation result.

In an exemplary embodiment, the types include: completely and strongly stained cells, incompletely and strongly stained cells, completely and weakly stained cells, incompletely and weakly stained cells, and non-stained cells.

In an exemplary embodiment, the quantity determining module 740 is configured to:

determine a quantity of elements in an intersection among the cell nucleus positions, the first region segmentation result, and the third region segmentation result as a quantity of the completely and strongly stained cells;

determine a quantity of elements in an intersection among the cell nucleus positions, a complementary set of the first region segmentation result with respect to the stained image under the $i^{th}$ field of view, and the second region segmentation result as a quantity of the incompletely and strongly stained cells;

determine a quantity of elements in an intersection among the cell nucleus positions, the first region segmentation result, a complementary set of the third region segmentation result with respect to the stained image under the $i^{th}$ field of view, and the second region segmentation result as a quantity of the completely and weakly stained cells;

determine a quantity of elements in an intersection among the cell nucleus positions, the complementary set of the first region segmentation result with respect to the stained image under the $i^{th}$ field of view, the complementary set of the third region segmentation result with respect to the stained image under the $i^{th}$ field of view, and the second region segmentation result as a quantity of the incompletely and weakly stained cells; and determine a quantity of elements in an intersection between the cell nucleus positions and a complementary set of the second region segmentation result with respect to the stained image under the $i^{th}$ field of view as a quantity of the non-stained cells, the cell membrane description result including the first region segmentation result, the second region segmentation result, and the third region segmentation result, the first region segmentation result being used for indicating the positions of the cell membranes with complete staining, the second region segmentation result being used for indicating the positions of the cell membranes whose staining intensities are greater than a first limit value, and the third region segmentation result being used for indicating the positions of the cell membranes whose staining intensities are greater than a second limit value.

In an exemplary embodiment, the cell nucleus detection module 720 is configured to process the stained image under the $i^{th}$ field of view by using a cell nucleus detection model to obtain the cell nucleus positions.

In an exemplary embodiment, the result determining module 750 is configured to:

determine proportions of the cells of types in the stained images under the n fields of view according to the quantities of the cells of types in the stained images under the n fields of view; and determine the analysis result of the pathological section according to the proportions of the cells of types.

When the apparatus provided in the foregoing embodiments implements functions of the apparatus, the division of the foregoing functional modules is merely an example for description. In the practical application, the functions may be assigned to and completed by different functional modules according to the requirements, that is, the internal structure of the device is divided into different functional modules, to implement all or some of the functions described above. In this application, the term "unit" or "module" refers to a computer program or part of the computer program that has a predefined function and works together with other related parts to achieve a predefined goal and may be all or partially implemented by using software, hardware (e.g., processing circuitry and/or memory configured to perform the predefined functions), or a combination thereof. Each unit or module can be implemented using one or more processors (or processors and memory). Likewise, a processor (or processors and memory) can be used to implement one or more modules or units. Moreover, each module or unit can be part of an overall module that includes the functionalities of the module or unit. In addition, the apparatus and method embodiments provided in the foregoing embodiments belong to the same conception. For the specific implementation process, reference may be made to the method embodiments, and details are not described herein again.

An exemplary embodiment of this application further provides an intelligent microscope system, including: a microscope, a camera, and a computer device.

The microscope is configured to observe a pathological section after cell membrane staining.

The camera is configured to obtain stained images, under n fields of view of the microscope, of the pathological section, n being a positive integer.

The computer device is configured to determine cell nucleus positions of cancer cells in a stained image under an $i^{th}$ field of view in the n fields of view, i being a positive integer less than or equal to n; generate a cell membrane description result of the stained image under the $i^{th}$ field of view, the cell membrane description result being used for indicating completeness and staining intensity of the cell membrane staining; determine quantities of cells of types in the stained image under the $i^{th}$ field of view according to the cell nucleus positions and the cell membrane description result; and determine an analysis result of the pathological section according to quantities of the cells of types in the stained images under the n fields of view.

In some embodiments, the computer device is further configured to perform other operations described in the foregoing method embodiments, and this is not limited in the embodiments of this application.

Figure 9:
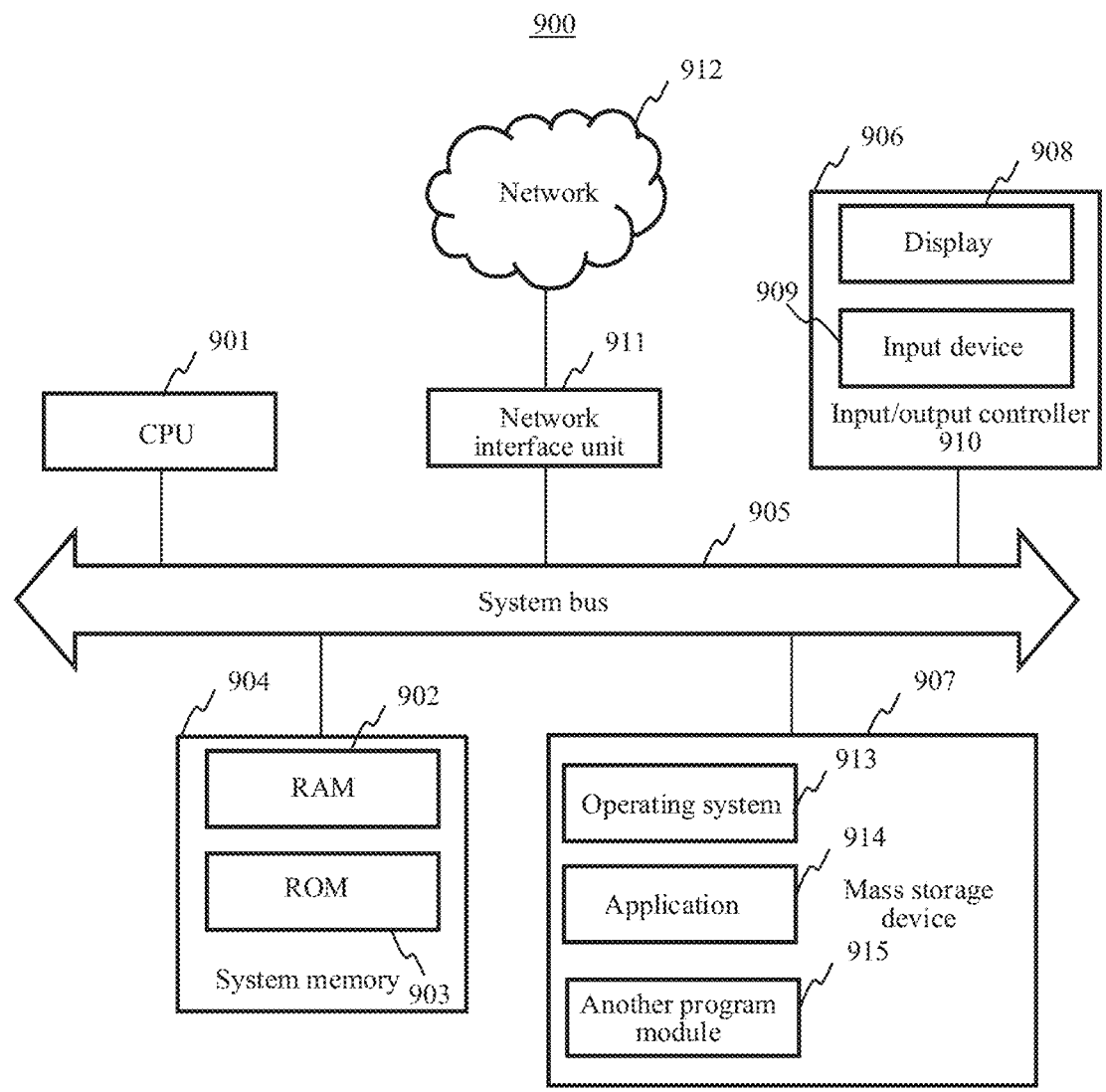
FIG. 9 is a schematic structural diagram of a computer device according to an embodiment of this application.

FIG. 9 is a schematic structural diagram of a computer device according to an embodiment of this application. Specifically, the computer device 900 includes a central processing unit (CPU) 901, a system memory 904 including a random access memory (RAM) 902 and a read only memory (ROM) 903, and a system bus 905 connecting the system memory 904 and the central processing unit 901. The computer device 900 further includes a basic input/output system (I/O) system 906 for facilitating information transmission between various devices in a computer and a mass storage device 907 configured to store an operating system 913, an application 914, and other application modules 915.

The basic input/output system 906 includes a display 908 configured to display information and an input device 909 such as a mouse and a keyboard for a user to input information. The display 908 and the input device 909 are both connected to the central processing unit 901 through an input/output controller 910 connected to the system bus 905. The basic input/output system 906 may further include the input/output controller 910 for receiving and processing input from a plurality of other devices such as a keyboard, a mouse, an electronic stylus, or the like. Similarly, the input/output controller 910 further provides output to a display screen, a printer, or other types of output devices.

The mass storage device 907 is connected to the central processing unit 901 through a mass storage controller (not shown) connected to the system bus 905. The mass storage device 907 and an associated computer-readable medium provide non-transitory storage for the computer device 900. That is, the mass storage device 907 may include a computer-readable medium (not shown) such as a hard disk or a compact disc ROM (CD-ROM) drive.

In general, the computer-readable medium may include a computer storage medium and a communication medium. The computer-storage medium includes volatile and non-transitory media, and removable and non-removable media implemented by using any method or technology used for storing information such as computer-readable instructions, data structures, program modules, or other data. The computer storage medium includes a RAM, a ROM, an erasable programmable ROM (EPROM), a flash memory or another solid-state storage technology, a CD-ROM, or another optical storage, a magnetic cassette, a magnetic tape, or a magnetic disk storage or another magnetic storage device. Certainly, those skilled in the art may learn that the computer storage medium is not limited to the above. The system memory 904 and the large-capacity storage device 907 may be collectively referred to as a memory.

According to the various embodiments of this application, the computer device 900 may further be connected, through a network such as the Internet, to a remote computer on the network for running. That is, the computer device 900 may be connected to a network 912 by using a network interface unit 911 connected to the system bus 905, or may be connected to another type of network or a remote computer system (not shown) by using a network interface unit 911.

The memory further includes at least one instruction, at least one program, a code set, or an instruction set. The at least one instruction, the at least one program, the code set, or the instruction set is stored in the memory and is configured to be executed by one or more processors to implement the foregoing pathological section image processing method.

In an exemplary embodiment, a computer-readable storage medium is further provided, the storage medium storing at least one instruction, at least one program, a code set, or an instruction set, the at least one instruction, the at least one program, the code set, or the instruction set, when executed by a processor of a terminal, implementing the foregoing pathological section image processing method.

In some embodiments, the computer-readable storage medium may include: a ROM, a RAM, a solid state drive (SSD), an optical disc, or the like. The RAM may include a resistance random access memory (ReRAM) and a dynamic random access memory (DRAM).

In an exemplary embodiment, a computer program product is further provided, the computer program product, when executed by a processor of a terminal, being used for implementing the foregoing pathological section image processing method.

It is to be understood that "plurality of" mentioned in this specification means two or more. "And/or" describes an association relationship for associated objects and represents that three relationships may exist. For example, A and/or B may represent the following three cases: only A exists, both A and B exist, and only B exists. The character "I" generally indicates an "or" relationship between the associated objects. In addition, the step numbers described in this specification merely schematically show a possible execution sequence of the steps. In some other embodiments, the steps may not be performed according to the number sequence. For example, two steps with different numbers may be performed simultaneously, or two steps with different numbers may be performed according to a sequence contrary to the sequence shown in the figure. This is not limited in the embodiments of this application.

The foregoing descriptions are merely exemplary embodiments of this application, but are not intended to limit this application. Any modification, equivalent replacement, or improvement made within the spirit and principle of this application shall fall within the protection scope of this application.

What is claimed is:

1. A pathological section image processing method performed by a computer device, the method comprising:

obtaining stained images of a pathological section, wherein each stained image is generated from a respective one of n fields of view of the pathological section under a microscope after cell membrane staining, n being a positive integer;

determining cell nucleus positions of cancer cells in a stained image under an $i^{th}$ field of view in the n fields of view, i being a positive integer less than or equal to n;

generating a cell membrane description result of the stained image under the $i^{th}$ field of view, the cell membrane description result being used for indicating completeness and staining intensity of the cell membrane staining;

determining quantities of cells of types in the stained image under the $i^{th}$ field of view according to the cell nucleus positions and the cell membrane description result; and determining an analysis result of the pathological section according to the quantities of the cells of types in the stained images under the n fields of view.

2. The method according to claim 1, wherein the generating a cell membrane description result of the stained image under the $i^{th}$ field of view comprises:

performing color channel decomposition and recombination on the stained image under the $i^{th}$ field of view to obtain a target stained channel image; and generating the cell membrane description result according to the target stained channel image, the cell membrane description result comprising a first region segmentation result, a second region segmentation result, and a third region segmentation result, the first region segmentation result being used for indicating positions of cell membranes with complete staining, the second region segmentation result being used for indicating positions of cell membranes whose staining intensities are greater than a first limit value, and the third region segmentation result being used for indicating positions of cell membranes whose staining intensities are greater than a second limit value.

3. The method according to claim 2, wherein the generating the cell membrane description result according to the target stained channel image comprises:

performing threshold segmentation processing on the target stained channel image by using a first threshold, to obtain a weakly-stained segmented image;

performing threshold segmentation processing on the target stained channel image by using a second threshold, to obtain a strongly-stained segmented image; and generating the cell membrane description result according to the weakly-stained segmented image and the strongly-stained segmented image.

4. The method according to claim 3, wherein the generating the cell membrane description result according to the weakly-stained segmented image and the strongly-stained segmented image comprises:

performing first morphological processing on the weakly-stained segmented image to obtain the first region segmentation result;

performing second morphological processing on the weakly-stained segmented image to obtain the second region segmentation result; and performing the second morphological processing on the strongly-stained segmented image to obtain the third region segmentation result.

5. The method according to claim 4, wherein the performing first morphological processing on the weakly-stained segmented image to obtain the first region segmentation result comprises:

performing cytoskeleton extraction processing on the weakly-stained segmented image to obtain a cytoskeleton in the weakly-stained segmented image;

searching for an enclosed region in which the cytoskeleton is closed;

filling, when the enclosed region is an innermost-layer enclosed region, the innermost-layer enclosed region to obtain an enclosed region segmented image; and extracting position information of foreground pixels in the enclosed region segmented image to obtain the first region segmentation result.

6. The method according to claim 4, wherein the performing second morphological processing on the weakly-stained segmented image to obtain the second region segmentation result comprises:

performing region expansion processing on the weakly-stained segmented image to obtain a processed weakly-stained segmented image; and extracting position information of foreground pixels in the processed weakly-stained segmented image to obtain the second region segmentation result.

7. The method according to claim 4, wherein the performing the second morphological processing on the strongly-stained segmented image to obtain the third region segmentation result comprises:

performing region expansion processing on the strongly-stained segmented image to obtain a processed strongly-stained segmented image; and extracting position information of foreground pixels in the processed strongly-stained segmented image to obtain the third region segmentation result.

8. The method according to claim 1, wherein the types comprise: completely and strongly stained cells, incompletely and strongly stained cells, completely and weakly stained cells, incompletely and weakly stained cells, and non-stained cells.

9. The method according to claim 8, wherein the determining quantities of cells of types in the stained image under the $i^{th}$ field of view according to the cell nucleus positions and the cell membrane description result comprises:

determining a quantity of elements in an intersection among the cell nucleus positions, the first region segmentation result, and the third region segmentation result as a quantity of the completely and strongly stained cells;

determining a quantity of elements in an intersection among the cell nucleus positions, a complementary set of the first region segmentation result with respect to the stained image under the $i^{th}$ field of view, and the second region segmentation result as a quantity of the incompletely and strongly stained cells;

determining a quantity of elements in an intersection among the cell nucleus positions, the first region segmentation result, a complementary set of the third region segmentation result with respect to the stained image under the $i^{th}$ field of view, and the second region segmentation result as a quantity of the completely and weakly stained cells;

determining a quantity of elements in an intersection among the cell nucleus positions, the complementary set of the first region segmentation result with respect to the stained image under the $i^{th}$ field of view, the complementary set of the third region segmentation result with respect to the stained image under the $i^{th}$ field of view, and the second region segmentation result as a quantity of the incompletely and weakly stained cells; and determining a quantity of elements in an intersection between the cell nucleus positions and a complementary set of the second region segmentation result with respect to the stained image under the $i^{th}$ field of view as a quantity of the non-stained cells, the cell membrane description result comprising the first region segmentation result, the second region segmentation result, and the third region segmentation result, the first region segmentation result being used for indicating the positions of the cell membranes with complete staining, the second region segmentation result being used for indicating the positions of the cell membranes whose staining intensities are greater than a first limit value, and the third region segmentation result being used for indicating the positions of the cell membranes whose staining intensities are greater than a second limit value.

10. The method according to claim 1, wherein the determining cell nucleus positions of cancer cells in a stained image under an $i^{th}$ field of view in the n fields of view comprises:

processing the stained image under the $i^{th}$ field of view by using a cell nucleus detection model to obtain the cell nucleus positions.

11. The method according to claim 1, wherein the determining an analysis result of the pathological section according to quantities of the cells of types in the stained images under the n fields of view comprises:

determining proportions of the cells of types in the stained images under the n fields of view according to the quantities of the cells of types in the stained images under the n fields of view; and determining the analysis result of the pathological section according to the proportions of the cells of types.

12. A computer device, comprising a processor and a memory, the memory storing at least one program, the at least one program being loaded and executed by the processor to perform a plurality of operations including:

obtaining stained images of a pathological section, wherein each stained image is generated from a respective one of n fields of view of the pathological section under a microscope after cell membrane staining, n being a positive integer;

determining cell nucleus positions of cancer cells in a stained image under an $i^{th}$ field of view in the n fields of view, i being a positive integer less than or equal to n;

generating a cell membrane description result of the stained image under the $i^{th}$ field of view, the cell membrane description result being used for indicating completeness and staining intensity of the cell membrane staining;

determining quantities of cells of types in the stained image under the $i^{th}$ field of view according to the cell nucleus positions and the cell membrane description result; and determining an analysis result of the pathological section according to the quantities of the cells of types in the stained images under the n fields of view.

13. The computer device according to claim 12, wherein the generating a cell membrane description result of the stained image under the $i^{th}$ field of view comprises:

performing color channel decomposition and recombination on the stained image under the $i^{th}$ field of view to obtain a target stained channel image; and generating the cell membrane description result according to the target stained channel image, the cell membrane description result comprising a first region segmentation result, a second region segmentation result, and a third region segmentation result, the first region segmentation result being used for indicating positions of cell membranes with complete staining, the second region segmentation result being used for indicating positions of cell membranes whose staining intensities are greater than a first limit value, and the third region segmentation result being used for indicating positions of cell membranes whose staining intensities are greater than a second limit value.

14. The computer device according to claim 12, wherein the types comprise: completely and strongly stained cells, incompletely and strongly stained cells, completely and weakly stained cells, incompletely and weakly stained cells, and non-stained cells.

15. The computer device according to claim 12, wherein the determining cell nucleus positions of cancer cells in a stained image under an $i^{th}$ field of view in the n fields of view comprises:

processing the stained image under the $i^{th}$ field of view by using a cell nucleus detection model to obtain the cell nucleus positions.

16. The computer device according to claim 12, wherein the determining an analysis result of the pathological section according to quantities of the cells of types in the stained images under the n fields of view comprises:

determining proportions of the cells of types in the stained images under the n fields of view according to the quantities of the cells of types in the stained images under the n fields of view; and determining the analysis result of the pathological section according to the proportions of the cells of types.

17. A non-transitory computer-readable storage medium, storing at least one program, the at least one program being loaded and executed by a processor of a computer device to perform a plurality of operations including:

obtaining stained images of a pathological section, wherein each stained image is generated from a respective one of n fields of view of the pathological section under a microscope after cell membrane staining, n being a positive integer;

determining cell nucleus positions of cancer cells in a stained image under an $i^{th}$ field of view in the n fields of view, i being a positive integer less than or equal to n;

generating a cell membrane description result of the stained image under the $i^{th}$ field of view, the cell membrane description result being used for indicating completeness and staining intensity of the cell membrane staining;

determining quantities of cells of types in the stained image under the $i^{th}$ field of view according to the cell nucleus positions and the cell membrane description result; and determining an analysis result of the pathological section according to the quantities of the cells of types in the stained images under the n fields of view.

18. The non-transitory computer-readable storage medium according to claim 17, wherein the generating a cell membrane description result of the stained image under the $i^{th}$ field of view comprises:

performing color channel decomposition and recombination on the stained image under the $i^{th}$ field of view to obtain a target stained channel image; and generating the cell membrane description result according to the target stained channel image, the cell membrane description result comprising a first region segmentation result, a second region segmentation result, and a third region segmentation result, the first region segmentation result being used for indicating positions of cell membranes with complete staining, the second region segmentation result being used for indicating positions of cell membranes whose staining intensities are greater than a first limit value, and the third region segmentation result being used for indicating positions of cell membranes whose staining intensities are greater than a second limit value.

19. The non-transitory computer-readable storage medium according to claim 17, wherein the determining cell nucleus positions of cancer cells in a stained image under an $i^{th}$ field of view in the n fields of view comprises:

processing the stained image under the $i^{th}$ field of view by using a cell nucleus detection model to obtain the cell nucleus positions.

20. The non-transitory computer-readable storage medium according to claim 17, wherein the determining an analysis result of the pathological section according to quantities of the cells of types in the stained images under then fields of view comprises:
   determining proportions of the cells of types in the stained images under the n fields of view according to the quantities of the cells of types in the stained images under the n fields of view; and
   determining the analysis result of the pathological section according to the proportions of the cells of types.

* * * * *